(12) United States Patent
Lokhorst et al.

(10) Patent No.: US 7,825,814 B2
(45) Date of Patent: Nov. 2, 2010

(54) BED OCCUPANT MONITORING SYSTEM

(75) Inventors: David M. Lokhorst, Victoria (CA); D. Robert Inkster, Victoria (CA)

(73) Assignee: Hill-Rom Services, Inc., Wilmington, DE (US)

( * ) Notice: Subject to any disclaimer, the term of this patent is extended or adjusted under 35 U.S.C. 154(b) by 0 days.

(21) Appl. No.: 12/017,605

(22) Filed: Jan. 22, 2008

(65) Prior Publication Data

US 2008/0132808 A1    Jun. 5, 2008

Related U.S. Application Data

(63) Continuation of application No. 10/521,024, filed as application No. PCT/CA03/01081 on Jul. 17, 2003, now abandoned.

(30) Foreign Application Priority Data

Jul. 17, 2002    (CA)    ..................................... 239880

(51) Int. Cl.
*G08B 23/00*    (2006.01)
(52) U.S. Cl. ..................................... 340/573.1; 340/575
(58) Field of Classification Search .............. 340/573.1; 600/301
See application file for complete search history.

(56) References Cited

U.S. PATENT DOCUMENTS

| | | |
|---|---|---|
| 3,802,417 A | 4/1974 | Lang |
| 3,961,201 A | 6/1976 | Rosenthal |
| 3,972,320 A | 8/1976 | Kalman |
| 4,020,482 A | 4/1977 | Feldl |
| 4,175,263 A | 11/1979 | Triplett et al. |
| 4,320,766 A * | 3/1982 | Alihanka et al. ............ 600/484 |
| 4,381,434 A | 4/1983 | Nichols |
| 4,633,237 A * | 12/1986 | Tucknott et al. ......... 340/573.4 |
| 4,745,647 A | 5/1988 | Goodwin |
| 4,839,512 A | 6/1989 | Speck |
| 4,907,845 A | 3/1990 | Wood |
| 5,144,284 A | 9/1992 | Hammett |
| 5,184,112 A | 2/1993 | Gusakov |
| 5,410,297 A | 4/1995 | Joseph et al. |
| 5,435,317 A | 7/1995 | McMahon et al. |
| 5,448,996 A | 9/1995 | Belin et al. |
| 5,479,932 A | 1/1996 | Higgins et al. |

(Continued)

FOREIGN PATENT DOCUMENTS

WO    WO9010281    9/1990

*Primary Examiner*—Toan N Pham
*Assistant Examiner*—Kerri McNally
(74) *Attorney, Agent, or Firm*—Barnes & Thornburg LLP

(57) ABSTRACT

The invention provides a bed occupant monitoring system comprising a pressure sensitive member attached to a support member for supporting a bed occupant, the pressure sensitive member comprising a plurality of pressure sensors. Each of the pressure sensors is configured to provide a reflected wave energy pressure signal by reflecting incident wave energy with an intensity which varies with a pressure applied to the sensor. A pair of fibers are coupled to each pressure sensor, each pair of fibers comprising an input fiber and an output fiber. The fibers are coupled to interface electronics comprising a wave energy source coupled to the input fiber of each of the pairs of fibers for providing the applied light energy, and, a wave energy detector coupled to the output fiber of each of the pairs of fibers for converting the scattered light energy into an electrical signal.

22 Claims, 10 Drawing Sheets

U.S. PATENT DOCUMENTS

| | | | |
|---|---|---|---|
| 5,558,996 A | | 9/1996 | Bartlett et al. |
| 5,654,694 A | | 8/1997 | Newham |
| 5,684,460 A | * | 11/1997 | Scanlon .................. 340/573.1 |
| 5,844,488 A | | 12/1998 | Musick |
| 5,917,180 A | * | 6/1999 | Reimer et al. .......... 250/227.14 |
| 5,993,400 A | * | 11/1999 | Rincoe et al. ............... 600/595 |
| 6,067,019 A | | 5/2000 | Scott |
| 6,134,970 A | | 10/2000 | Kumakawa et al. |
| 6,208,250 B1 | | 3/2001 | Dixon et al. |
| 6,280,392 B1 | | 8/2001 | Yoshimi et al. |
| 6,468,234 B1 | | 10/2002 | Van de Loos et al. |
| 6,498,652 B1 | * | 12/2002 | Varshneya et al. .......... 356/477 |
| 6,544,200 B1 | | 4/2003 | Smith et al. |
| 6,687,424 B1 | | 2/2004 | Gerdt et al. |
| 6,721,980 B1 | | 4/2004 | Price et al. |
| 6,791,460 B2 | | 9/2004 | Dixon et al. |
| 6,897,780 B2 | | 5/2005 | Ulrich et al. |
| 6,917,293 B2 | | 7/2005 | Beggs |
| 2001/0001235 A1 | | 5/2001 | Menkedick et al. |
| 2002/0010390 A1 | * | 1/2002 | Guice et al. .................. 600/300 |
| 2002/0014968 A1 | | 2/2002 | Fitzgerald et al. |
| 2002/0067273 A1 | | 6/2002 | Jaques et al. |
| 2002/0080037 A1 | * | 6/2002 | Dixon et al. ............. 340/573.1 |
| 2002/0196148 A1 | * | 12/2002 | Nunome .................. 340/573.1 |

* cited by examiner

BED OCCUPANT MONITORING SYSTEM

CROSS REFERENCES

This application is a continuation of pending U.S. patent application Ser. No. 10/521,024, which is the United States national stage application under 35 U.S.C. §371(c) of Patent Cooperation Treaty Application No. PCT/CA2003/001081, filed Jul. 17, 2003, which claims priority under 35 U.S.C. §119(a) to Canadian Patent Application No. 239880, filed Jul. 17, 2002, and all of such prior applications are incorporated herein by this reference.

TECHNICAL FIELD

This invention relates to monitoring the health and/or activity of a person occupying a bed. This invention provides a novel system comprising a pressure sensitive member coupled to interface electronics.

BACKGROUND

It is known to use sensors coupled to a mattress for monitoring a bed occupant. For example, Triplett et al. (U.S. Pat. No. 4,175,263) disclose a pressure sensing mechanism for placement on a hospital bed. The pressure sensing mechanism comprises a first pressure sensing pad for sensing a patient's weight when the patient is near the centre of the bed, and a second pressure sensing pad for sensing the patient's weight when the patient is near the edges of the bed. An alarm may be triggered when the patient moves to a location near the edge of the bed.

Tucknott et al. (U.S. Pat. No. 4,633,237) disclose a patient bed alarm system comprising a matrix of sensors woven into a mat for placement on a bed. The matrix of sensors is coupled to a micro computer for calculating the position of a patient in the bed. An alarm may be triggered when the patient is about to leave the bed.

Alihanka et al. (U.S. Pat. No. 4,320,766) disclose a capacitive motion sensor placed under a mattress or the like for monitoring the movements of a person.

McMahon et al. (U.S. Pat. No. 5,435,317) disclose a device for detecting a respiratory dysfunction of a person located in a bed. The device comprises a detection unit which is provided under the mattress of the bed, and a stimulation unit, which acts, in response to a signal from the detection unit, to impart a rocking motion to the bed. The detection unit is embodied as a pad-like device provided under the mattress.

Bellin et al. (U.S. Pat. No. 5,558,996) disclose a patient monitoring device wherein sensors are located in a bed sheet with which a subject comes in contact. One sensor produces a signal corresponding to respiratory induced, pulmonary motion, and myocardial pumping sounds. A second sensor produces a signal corresponding to changes in body position. A processor amplifies and filters the induced signals resulting in resolved output highly correlated to respiration rate, heart beat rate, and changes in body position.

Reimer et al. (U.S. Pat. No. 5,917,180) disclose a pressure sensor which relies on detecting multiply scattered light within an optical cavity. Changes in the volume of the cavity are sensed by the change in sampled light intensity. Pressure sensitive mats with a high density of sensors are assembled using optical fiber technology.

Musick (U.S. Pat. No. 5,844,488) discloses a narrow, pressure-sensitive sensor pad for installation on top of and across the width of a mattress proximate the midsection of a reclining patient. The pad has both central and edge switching areas. The central pressure sensitive switch indicates the presence of a patient in the center of the bed. When a patient moves toward either edge of the bed, an edge switch is activated which generates an early warning signal indicating to attending personnel that a patient has moved from the center of the bed to an edge and may be attempting to exit the bed unattended.

Hammett (U.S. Pat. No. 5,144,284) discloses a bed covering device adapted to cover a mattress. The device has compliant flat pressure sensitive means disposed its lower surface for detecting compressive force exerted by a person, and electrical connector means emergent from the pressure sensitive means and configured to connect in modular fashion with a monitoring device and alarm.

Rudeke (PCT publication No. WO9010281A1) discloses a bed alarm intended for use with patients in hospitals and like establishments for indicating when a patient leaves his or her bed. The alarm includes a pressure sensor which functions to detect whether a patient is lying in bed or not and which is intended to be positioned in the bed and preferably between the bed-bottom and the mattress.

Rincoe et al. (U.S. Pat. No. 5,993,400) and Scott (U.S. Pat. No. 6,067,019) disclose devices that utilize arrangements of sensors to detect the impending egress of a bed occupant. Joseph et al. (U.S. Pat. No. 5,410,297) disclose a weight-sensitive capacitive sensor for tracking the position of an occupant. Dixon et al. (U.S. Pat. No. 6,208,250) disclose a system comprising two sensors and a processor used to determine the location of a patient on a bed.

Rosenthal (U.S. Pat. No. 3,961,201) discloses a switch located between a mattress and a bedframe that is used to detect when a patient moves close to the edge of a bed. Feldl (U.S. Pat. No. 4,020,482) discloses an air bladder below a mattress that signals egress of a patient when air pressure in the bladder falls below a threshold. Nicholas (U.S. Pat. No. 4,381,434) discloses a device including a spring-loaded plate with a limit switch, all mounted below a mattress.

Despite the volume of existing patent literature, there are significant shortcomings in the known devices. For many devices, reliable operation requires installation on top of the mattress. This has two major shortcomings: firstly, the devices are often stiff (i.e. resistant to flexing) and hard, thereby causing discomfort to the bed occupant. In some applications (for example, monitoring of demented occupants) this can cause physical and psychological irritation to the bed occupant. Secondly, because the devices are on top of the mattress, they rapidly suffer material fatigue and fail under normal use.

SUMMARY OF INVENTION

One embodiment of the invention provides a bed occupant monitoring system comprising a pressure sensitive member coupled to a support member for supporting a bed occupant, the pressure sensitive member comprising a plurality of pressure sensors. Each of the pressure sensors is configured to provide an optical pressure signal having an intensity which varies with a pressure applied thereto. The monitoring system also includes at least one wave energy source coupled to the plurality of pressure sensors for providing wave energy to the sensors, and, at least one wave energy detector coupled to the plurality of pressure sensors for converting the optical pressure signals into electrical pressure signals.

The wave energy source may coupled to the plurality of pressure sensors by means of optical fibres, and the wave energy detector may also coupled to the plurality of pressure sensors by means of optical fibres. An indicator device may be coupled to the interface electronics.

The wave energy detector may comprise a photodetector. The photodetector may comprise an array of photo-diodes, and each of the photo-diodes may be coupled to one of the plurality of pressure sensors by means of an optical fibre.

The interface electronics may further comprise threshold circuitry for comparing the electrical pressure signals to a predetermined threshold. The threshold circuitry may comprise a threshold comparer for determining if the electrical pressure signals are below the predetermined threshold. The threshold circuitry may further comprise a threshold crossing detector configured to reset a timer when the electrical pressure signals cross the predetermined threshold. The system may further comprise an alarm signal generator coupled to the timer and the threshold comparer by means of an AND gate, the alarm signal generator configured to generate an alarm signal if the timer is not reset for a predetermined time period and the electrical pressure signals are below the predetermined threshold.

The pressure sensitive member may comprise a top foam layer and a bottom foam layer, and each pressure sensor may be formed by securing a pair of optical fibres between the top foam layer and the bottom foam layer, the pair of optical fibres comprising an input fibre coupled to the wave energy source and an output fibre coupled to the wave energy detector.

The pressure sensitive member may comprise an area of a mattress constructed from a compressible material, and each pressure sensor may be formed by securing a pair of optical fibres between the top foam layer and the bottom foam layer, the pair of optical fibres comprising an input fibre coupled to the wave energy source and an output fibre coupled to the wave energy detector.

Each of the pressure sensors may be responsive to pressure in a range of 1 to 15 mmHg.

The support member may comprise a mattress, and the pressure sensitive member may be positioned atop the mattress, below the mattress, within a cavity in the mattress, in a recess near a top of the mattress, such that a top surface of the pressure sensitive member is flush with a top surface of the mattress, or in a recess near a bottom of the mattress, such that a bottom surface of the pressure sensitive member is flush with a bottom surface of the mattress.

The plurality of pressure sensors may be arranged in an array across a width of the support member, and the interface electronics may comprise signal processing means for determining a position of the occupant on the support member. The plurality of pressure sensors may be arranged into a central group and two side groups, with the side groups positioned adjacent to edges of the support member and the central group positioned therebetween, and the signal processing means are configured to calculate a total applied pressure for each group.

The monitoring system may further comprise an opaque covering material for shielding the pressure sensors from ambient light.

The monitoring system may further comprise a protective sheath covering the optical fibres between the pressure sensitive member and the interface electronics.

Another embodiment of the invention provides a method of monitoring a bed occupant occupying a bed with a pressure sensitive member coupled thereto, the pressure sensitive member comprising a plurality of pressure sensors, each of the pressure sensors configured to provide a reflected wave energy pressure signal by reflecting incident wave energy with an intensity which varies with a pressure applied thereto.

The method comprises applying wave energy to the pressure sensors, and, measuring pressure signals received from the pressure sensitive member.

The method may comprise processing the measured pressure signals by taking a sum of a time derivative of the absolute values of the pressure signals, taking a sum of a time derivative of the pressure signals, or taking a sum of a time derivative of the squared pressure signals.

The method may comprise comparing the measured pressure signals to a predetermined threshold. The method may comprise generating an alarm signal if the measured pressure signals remain below the predetermined threshold for a predetermined time period. The predetermined threshold and predetermined time period may be set in relation to an expected heat beat pressure signal, an expected pulmonary pressure signal, or an expected bodily movement pressure signal.

The method may comprise computing a heart rate of the bed occupant from the measured pressure signals, and/or computing a respiration rate of the bed occupant from the measured pressure signals.

Another embodiment of the invention provides a bed occupant monitoring system comprising a pressure sensitive member coupled to a support member for supporting a bed occupant, the pressure sensitive member comprising a plurality of pressure sensors, interface electronics coupled to the pressure sensors for producing at least one pressure signal; and, threshold circuitry for comparing the pressure signals to a predetermined threshold.

BRIEF DESCRIPTION OF DRAWINGS

In drawings which illustrate non-limiting embodiments of the invention.

DESCRIPTION

Throughout the following description specific details are set forth in order to provide a more thorough understanding of the invention. However, the invention may be practiced without these particulars. In other instances, well known elements have not been shown or described in detail to avoid unnecessarily obscuring the present invention. Accordingly, the specification and drawings are to be regarded in an illustrative, rather than a restrictive, sense.

The invention provides apparatus and methods for monitoring a bed occupant, such as a patient, lying in a bed. Apparatus according to the invention can facilitate monitoring of the bed occupant's presence, heart rate, respiration, and/or movement. The apparatus comprises a pressure sensitive member in the bed coupled to interface electronics. The pressure sensitive member preferably comprises an array of pressure sensors which produce signals representative of the pressures applied to the sensors.

Figure 1:
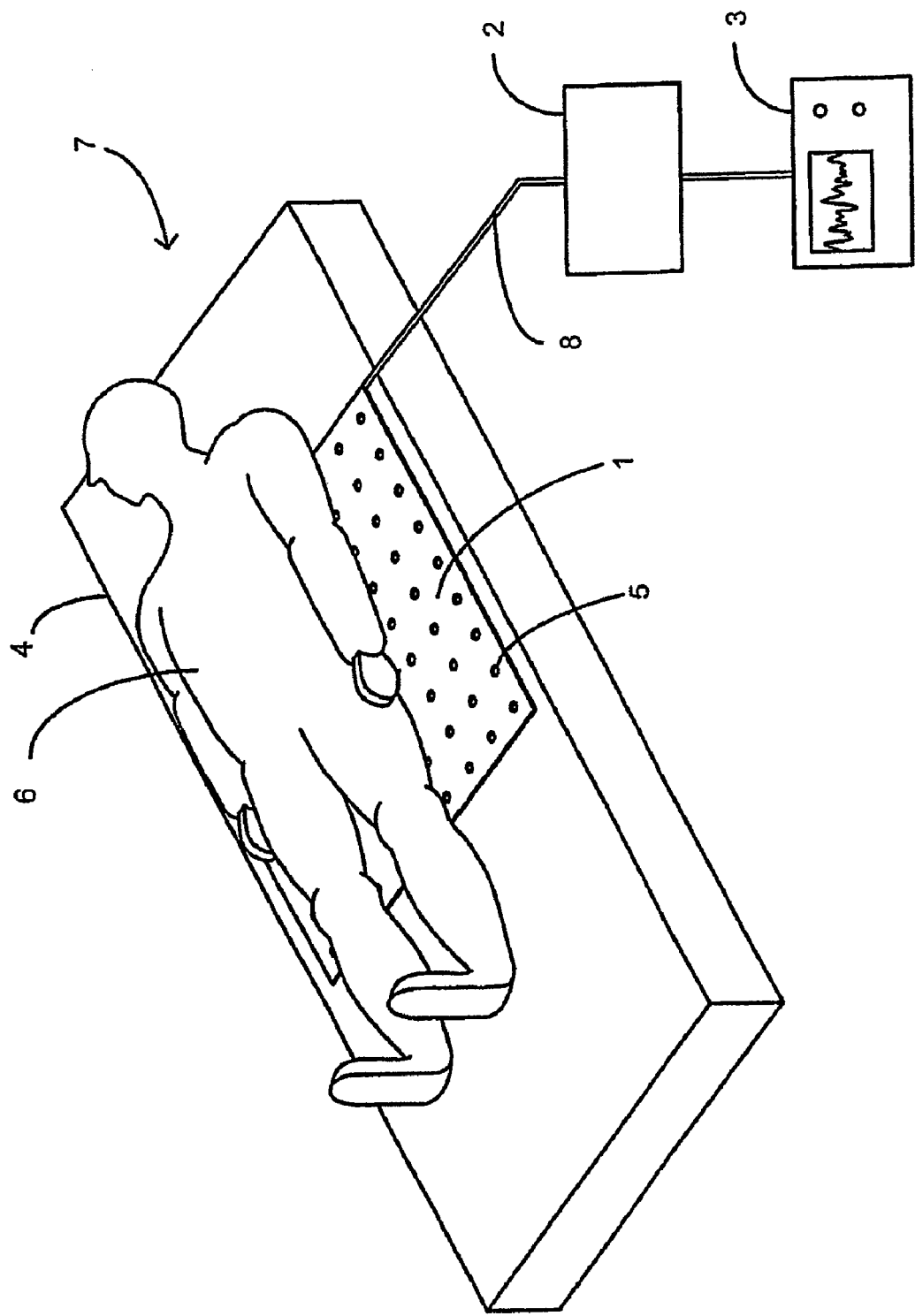
FIG. 1 illustrates schematically an occupant lying in a bed equipped with a monitoring system according to one embodiment of the invention.

FIG. 1 is a schematic view of a bed occupant monitoring system 7 according to one embodiment of the invention. A bed occupant 6 lies upon a bed which includes a mattress or other support member 4. Monitoring system 7 includes a pressure sensitive member 1 on support member 4. Pressure sensitive member 1 is coupled to interface electronics 2 by signal carriers 8. Signal carriers 8 may comprise optical fibres, wires or other signal carriers capable of carrying signals from pressure sensors 5 in pressure sensitive members 1 to interface electronics 2.

Interface electronics 2 may be housed in a single enclosure as illustrated in FIG. 1, or they may be housed in more than one enclosure connected by signal means (not shown). The signal means may comprise any suitable signal carriers, for example, one or more wires, optical signal carriers, wireless connections, or the like. Optionally, interface electronics 2 comprises an indicator device 3. Indicator device 3 may comprise an visible or audible alarm, a data display system, an attendant call system, a data logging system, or the like.

Pressure sensitive member 1 comprises a plurality of pressure sensors 5. Each pressure sensor 5 measures the bearing pressure applied by occupant 6 in proximity thereto. A change in the bearing pressure results in a change in the output of pressure sensor 5. Pressure sensors 5 are preferably responsive to pressures in the range of 1 to 15 mmHg. Pressure sensors 5 preferably comprise pressure sensors which produce optical output signals. Most preferably the pressure sensors are optical sensors which do not require any electrical or electronic devices to be at the location of the sensor. The term "optical", as used herein, is to be understood to refer to electromagnetic wave energy of any wavelength, and not only to those wavelengths which correspond to the visible spectrum. Optical pressure sensors are advantageous because they allow monitoring of occupant 6 without the need for electrical devices in the bed, which may be hazardous.

Pressure sensors 5 may be constructed in accordance with U.S. Pat. No. 5,917,180 to Reimer et al., which is hereby incorporated by reference. Such sensors are available under the brand name Kinotex™ from Tactex Controls Inc. of Victoria, British Columbia, Canada. Such sensors are particularly advantageous for bed occupant monitoring as they exhibit a high level of sensitivity to minor pressure variations over a wide range of pressure levels. Conventional pressure sensors with comparable sensitivity typically will be unable to sense minor pressure variations at elevated pressure levels, such as when a person is lying or sitting upon them.

In certain specific embodiments of the invention, each pressure sensor 5 is configured to reflect incident wave energy received from interface electronics 2 with an intensity which varies with a pressure applied to pressure sensor 5. In such embodiments, signal carriers 8 comprise a plurality of pairs of fibres, with one pair coupled to each pressure sensor 5. Each pressure sensor is coupled to interface electronics 2 by an input fibre 15 (see FIG. 2), which provides incident wave energy, and an output fibre 14 (see FIG. 2), which transmits reflected wave energy to interface electronics 2.

As described in Reimer et al., Kinotex™ pressure sensors utilize an optical-to-electronic interface. The optical-to-electronic interface comprises one or more wave energy sources, typically light transmitters (such as one or more light-emitting-diodes) and one or more wave energy detectors, typically photodetectors (such as one or more photo-diodes or phototransistors). Interface electronics 2 includes the optical-to-electronic interface.

In one embodiment of this invention, the optical-to-electronic interface comprises one light emitter and one photodetector, and the interface electronics comprise analog and/or digital circuit elements configured to provide an output signal representative of the total pressure applied to pressure sensitive member 1. In another embodiment, the optical-to-electronic interface comprises at least one light emitter and more than one photodetector, and the signal conditioning electronics comprise analog and/or digital circuit elements configured to provide multiple output signals representative of the pressures applied to different regions of the pressure sensitive member, as discussed below with reference to FIG. 10.

In another embodiment of the invention, the interface electronics are configured to measure signals from each of the pressure sensors individually. Alternatively (or additionally) further circuit elements may be included to extract other information from the signals, such as the time-derivative (i.e. time rate of change) of the signal or a high-pass filter or a low-pass filter or a notch filter or any combination of the foregoing. Each of these provides valuable information regarding the condition of the bed occupant.

Although it is possible in principle to implement the invention using entirely analog electronics, it is preferable to use a combination of analog, optical and digital electronics. The signal processing function of interface electronics 2 may be provided in hardware, in software, or in a combination of hardware and software. Standard signal processing techniques may be used to increase the signal to noise ratio of such signals and to extract desired information from the signals.

Figure 2:
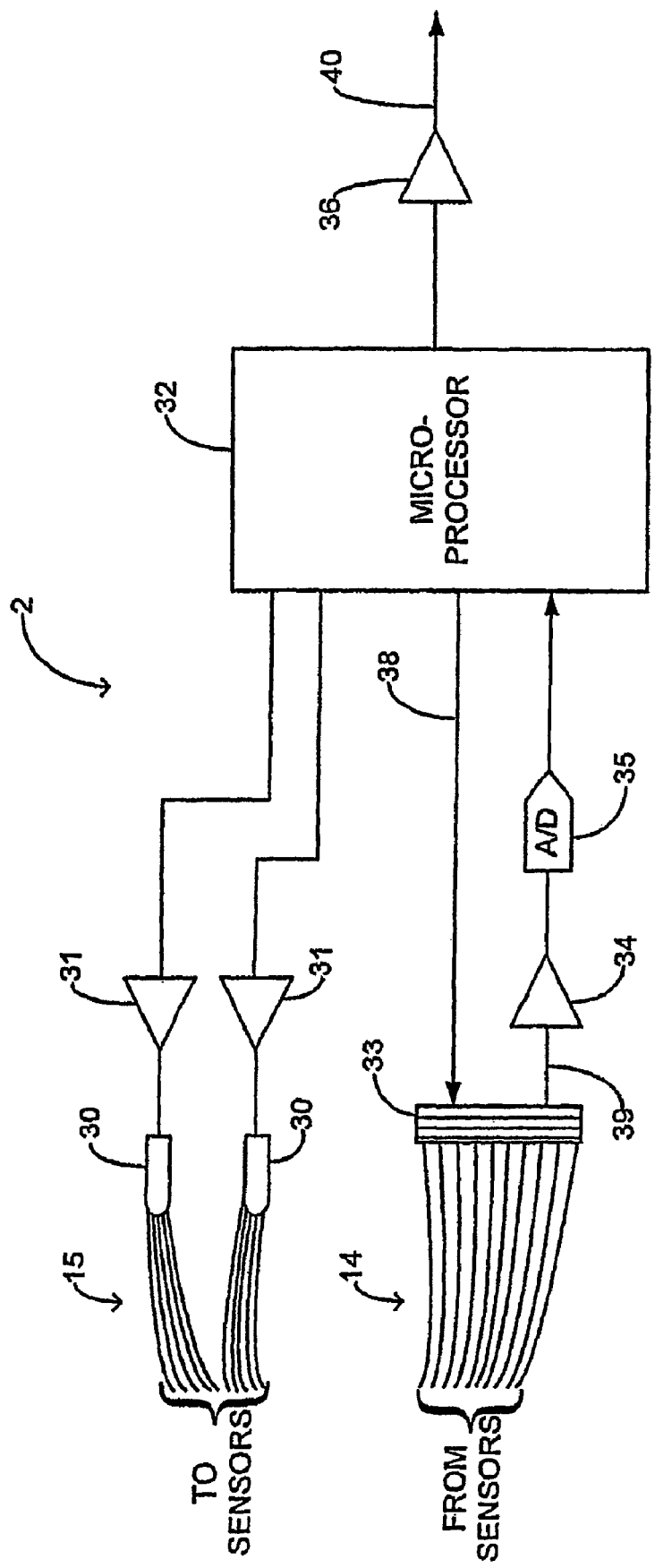
FIG. 2 illustrates schematically interface electronics according to an embodiment of the invention.

As an example of a preferred embodiment, a simplified schematic illustration of interface electronics 2 is shown in FIG. 2. A microprocessor 32 is coupled to two LED drive circuits 31 that provide current to two LEDs 30. LEDs 30 provide illumination for pressure sensors 5. Although two LEDs 30 and LED drive circuits 31 are shown in FIG. 2 for ease of illustration, it is to be understood that any number of LEDs 30 and drive circuits 31 are possible. An input fibre 15 provides light energy from LEDs 30 to each of pressure sensors 5 (not shown in FIG. 2). An output fibre 14 returns light from each pressure sensor 5 (not shown in FIG. 2) to photodetector 33. Photodetector 33 preferably comprises an array of photo-diodes, with each receiving fibre 14 being associated with a specific photo-diode.

Microprocessor 32 provides control signals 38 that cause photodetector 33 to output an analog signal 39 corresponding to the light intensities received from pressure sensors 5. In the illustrated embodiment, control signals 38 are used to coordinate the signals being sent from the individual elements of photodetector 33 to microprocessor 32 when photodetector 33 comprises an array of photo-diodes or other sensors. Alternatively, photodetector 33 could be configured to provide a separate analog signal 39 to microprocessor 32 from each element of photodetector 33. In the further alternative, monitoring system 7 could include a signal concentrator (not shown) which combines signals from two or more pressure sensors 5 and provides microprocessor 32 with a signal indicating a property of the combined signals, for example a signal containing information about an average pressure exerted on the two or more pressure sensors 5. The signals may be combined optically, for example by detecting light from multiple pressure sensors 5 at a single light detector, or may be combined electronically after having been detected.

Optionally, analog signal 39 may be amplified, filtered, or otherwise conditioned by analog circuitry 34. Analog signal 39 is then converted into digital form by Analog-to-Digital converter 35, and the sampled signal is read by microprocessor 32. Microprocessor 32 implements any necessary signal processing, as described below, and produces output signals 40 via appropriate driver circuitry 36. Driver circuitry 36 may optionally comprise well known electronic interfaces such as RS-232, RS-485, Ethernet, Universal Serial Bus, or the like, or a digitally controlled driver. Output signal 40 may be passed to an indicator device 3 (not shown in FIG. 2), a remote monitoring station, an automated alarm system, or the like. Monitoring system 7 may be used to monitor various indications of health of bed occupant 6, including the pulmonary and/or heart activity of bed occupant 6. Referring again to FIG. 2, interface electronics 2 may produce an output signal 40 representative of any of the following parameters: the sum of the time derivative of all pressure signals; the sum of the time derivative of the squared pressure signals; or, the sum of the time derivative of the absolute values of the pressure signals. Output signal 40 may comprise a digital, analog or optical signal. The inventors have found that the pulmonary activity, heart activity, and bodily movement of the bed occupant can be determined from these computed parameters.

Figure 3:
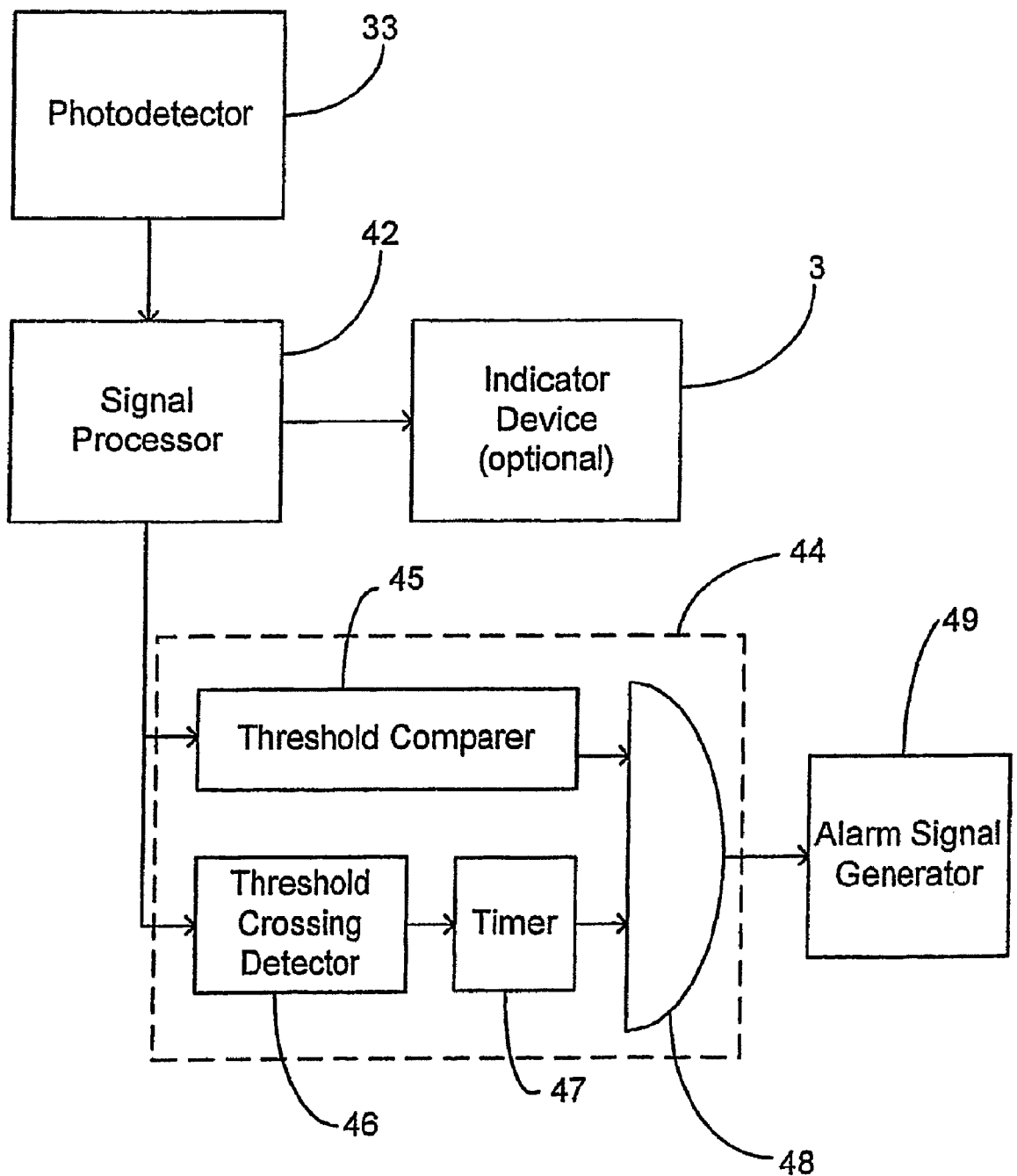
FIG. 3 is a block diagram of some circuit elements of interface electronics according to another embodiment of the invention.

FIG. 3 shows one possible arrangement of functional characteristics of interface electronics 2. Photodetector 33 provides pressure signals to signal processor 42. Signal processor 42 amplifies, takes the time derivative, or otherwise processes the pressure signals, and passes them to threshold circuitry 44, and optionally also to indicator device 3. Threshold circuitry 44 preferably comprises threshold comparer 45, threshold crossing detector 46, and timer 47. Threshold comparer 45 is configured to produce a signal indicating when the pressure signals indicate a pressure below a predetermined threshold. Threshold crossing detector 46 is configured to reset timer 47 when the pressure signals cross the threshold. Timer 47 is configured to produce a high output if allowed to run without for a predetermined time period without being reset. AND gate 48 is configured to trigger alarm signal generator 49 when it receives high outputs from both threshold comparer 45 and timer 47. Threshold circuitry 44 may be configured to monitor a number of different thresholds, as described below.

Figure 4:
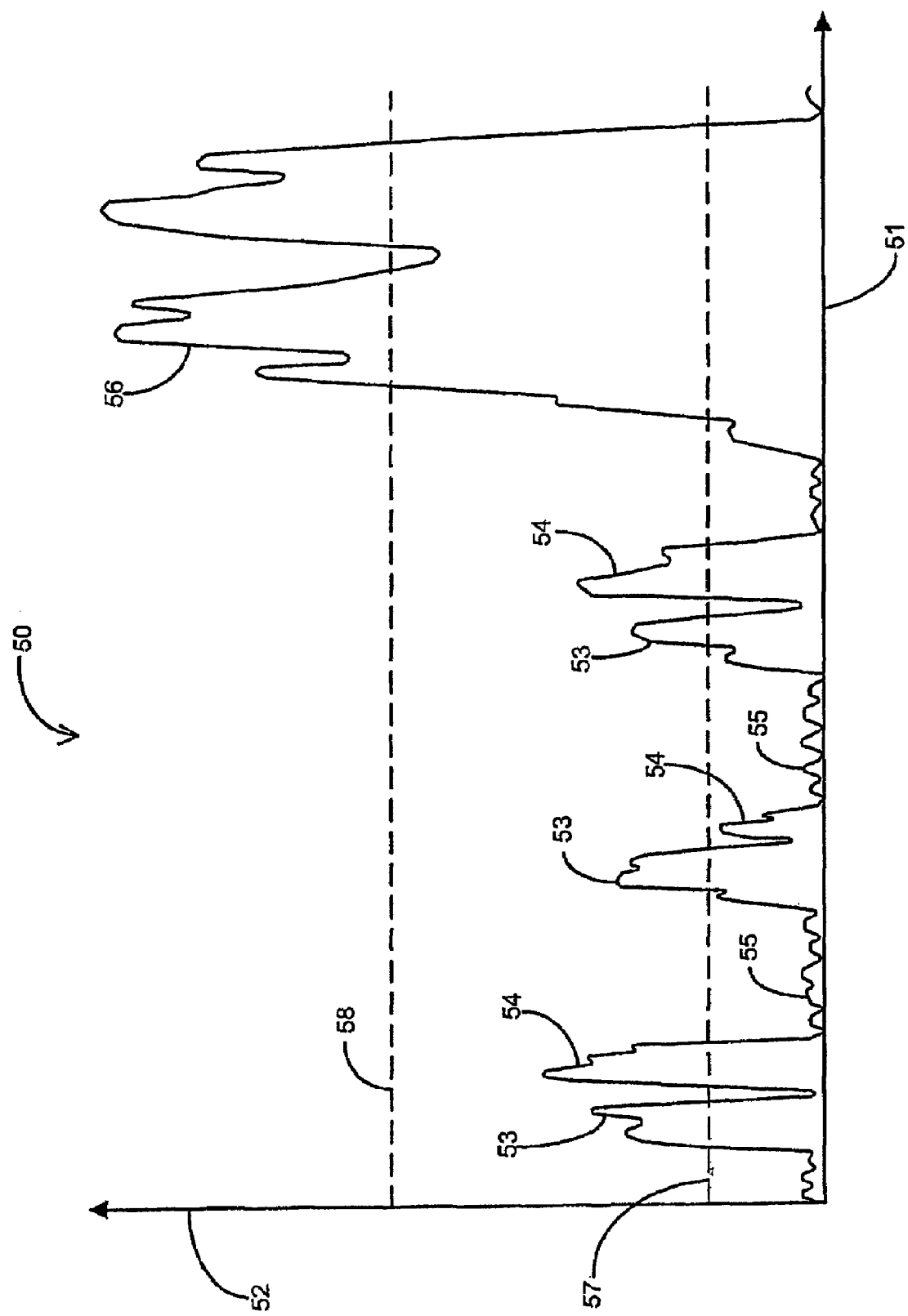
FIG. 4 graphically depicts externally applied pressure over time for an example situation of a patient occupying a bed equipped with a monitoring system according to the invention.

FIG. 4 is a typical graph 50 of the sum of the derivatives of the absolute value of the pressure signals generated by a bed occupant lying in a bed equipped with a monitoring system according to the invention, plotted against time. Graph 50 is an idealized representation of pressure signals generated by a pressure sensitive member 1 located on top of support member 4. The variations in the pressure signals are typically less pronounced when the signals are generated by a pressure sensitive member 1 located within or below support member 4, and as such it may be difficult to determine the heart rate of bed occupant 6, although pulmonary activity and movement may still be detected, as described below. It is to be understood that a graph of actual pressure signals may include more noise than illustrated, but the noise may be minimized by any suitable noise reduction techniques.

In graph 50, time is indicated from left to right, along axis 51. Peaks 53 and 54 correspond to inhaling and exhaling respectively. The smaller more frequent peaks 55 correspond to heat beats. The large disturbance 56 corresponds to bodily movement (for example, when the bed occupant shifts his weight). Movement signals 56 are typically on the order of ten times larger than pulmonary signals 53 and 54, which are in turn typically on the order of ten times larger than heart beat signals 55. The pressure signals will only remain constant if the bed occupant's heart stops beating, the bed occupant leaves the bed, or there is a malfunction. Interface electronics 2 may be configured to generate an alarm signal if the pressure signals remain below a heart beat threshold for a predetermined period of time selected according to an expected heart beat frequency, or if the pressure signals remain constant for a predetermined period of time. Further signal processing can optionally be performed by signal processing means in interface electronics 2 to measure the precise rate of respiration and/or the rate of heart beat from the signal shown in FIG. 4. The signal processing means may comprise microprocessor 32, a digital signal processor, and/or noise reduction circuitry.

In one embodiment of the invention, a pulmonary threshold 57 may be set such that if the signal remains below pulmonary threshold 57 for a predetermined period of time, output signal 40 includes a pulmonary alarm which indicates the suspension of pulmonary activity. The predetermined amount of time for the pulmonary alarm may be set according to an expected respiratory frequency. Pulmonary threshold 57 may be determined adaptively by microprocessor 32 based on the pattern of measured pressure signals, or may be preset when monitoring system 7 is manufactured and calibrated. Optionally, a user interface (not shown) may be provided to allow pulmonary threshold 57 and the time period for the pulmonary alarm to be adjusted to allow for differences in weights and breathing patterns of different bed occupants.

In another embodiment, a bodily movement threshold 58 can be set such that if the signal remains below movement threshold 58 for a predetermined period of time, output signal 40 includes a pulmonary alarm which indicates the suspension of pulmonary activity. The predetermined time period for the movement alarm is set so that the alarm will sound before bed occupant 6 has remained motionless for so long as to be at risk for bed sores. Movement threshold 58 may be determined adaptively by microprocessor 32 based on the pattern of measured pressure signals, or may be preset when monitoring system 7 is manufactured and calibrated. Optionally, a user interface (not shown) may be provided to allow movement threshold 58 and the time period for the movement alarm to be adjusted to allow for differences in weights and movement patterns of different bed occupants.

Figure 5:
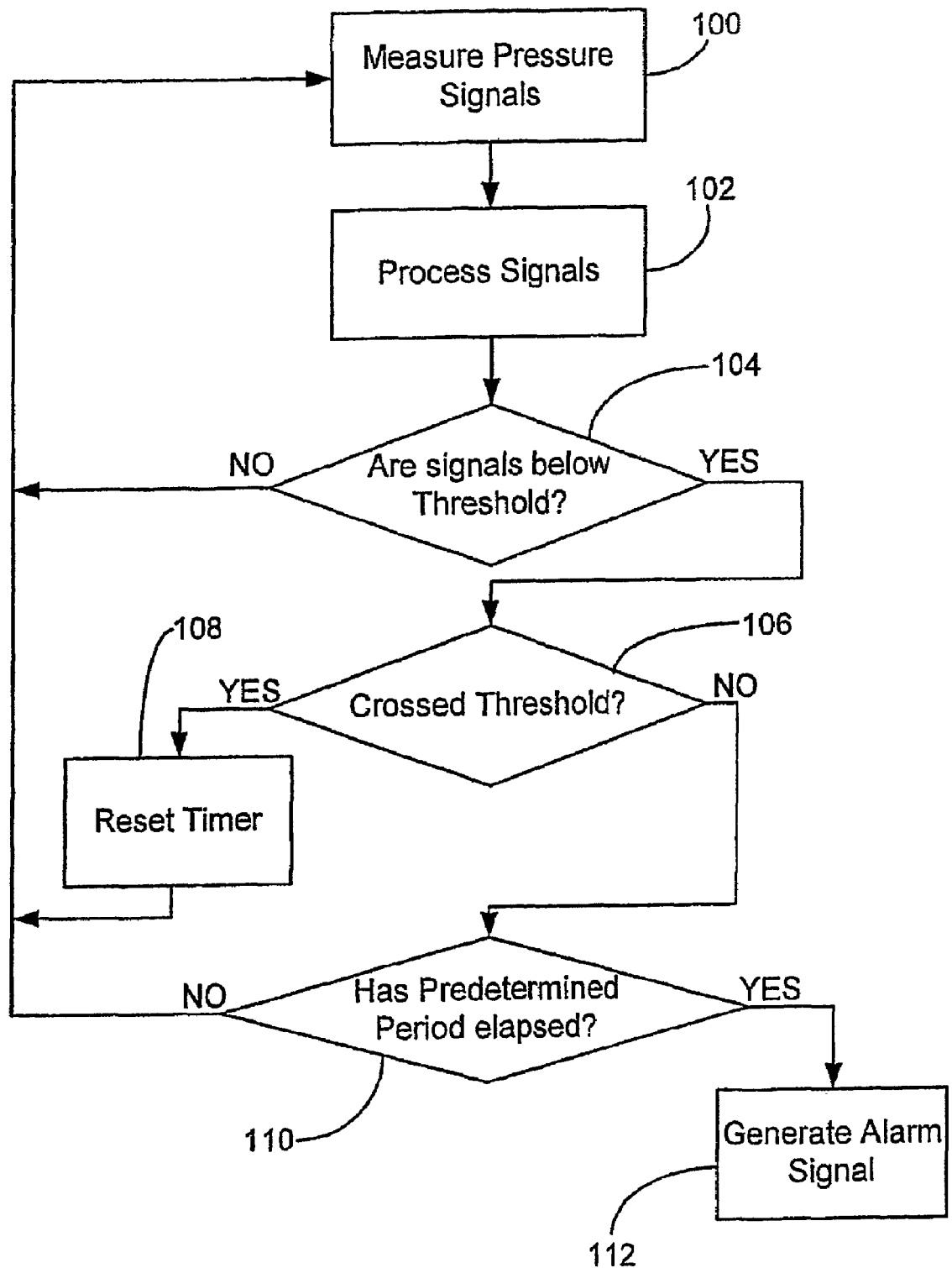
FIG. 5 is a flowchart illustrating a method of monitoring a bed occupant according to one embodiment of the invention.

FIG. 5 is a flowchart illustrating a method of monitoring a bed occupant according to one embodiment of the invention. At block 100, pressure signals are measured by photodetector 33. At block 102, the measured signals are processed by signal processor 42. At block 104, the signals are compared to a threshold by threshold comparer 45. If the signals are not below the threshold (block 104 NO output), the method returns to block 100. If the signals are below the threshold (block 104 YES output), the method continues to block 106. At block 106, threshold crossing detector 46 determines whether the signals have just crossed the threshold. If they have (block 106 YES output), timer 47 is reset at block 108 and the method returns to block 100. If they have not (block 106 NO output) the method continues to block 110. At block 110, if timer 47 has been running for a predetermined period since it was last reset (block 110 YES output), an alarm signal is generated at block 112. If not, (block 110 NO output), the method returns to block 100.

Figure 6:
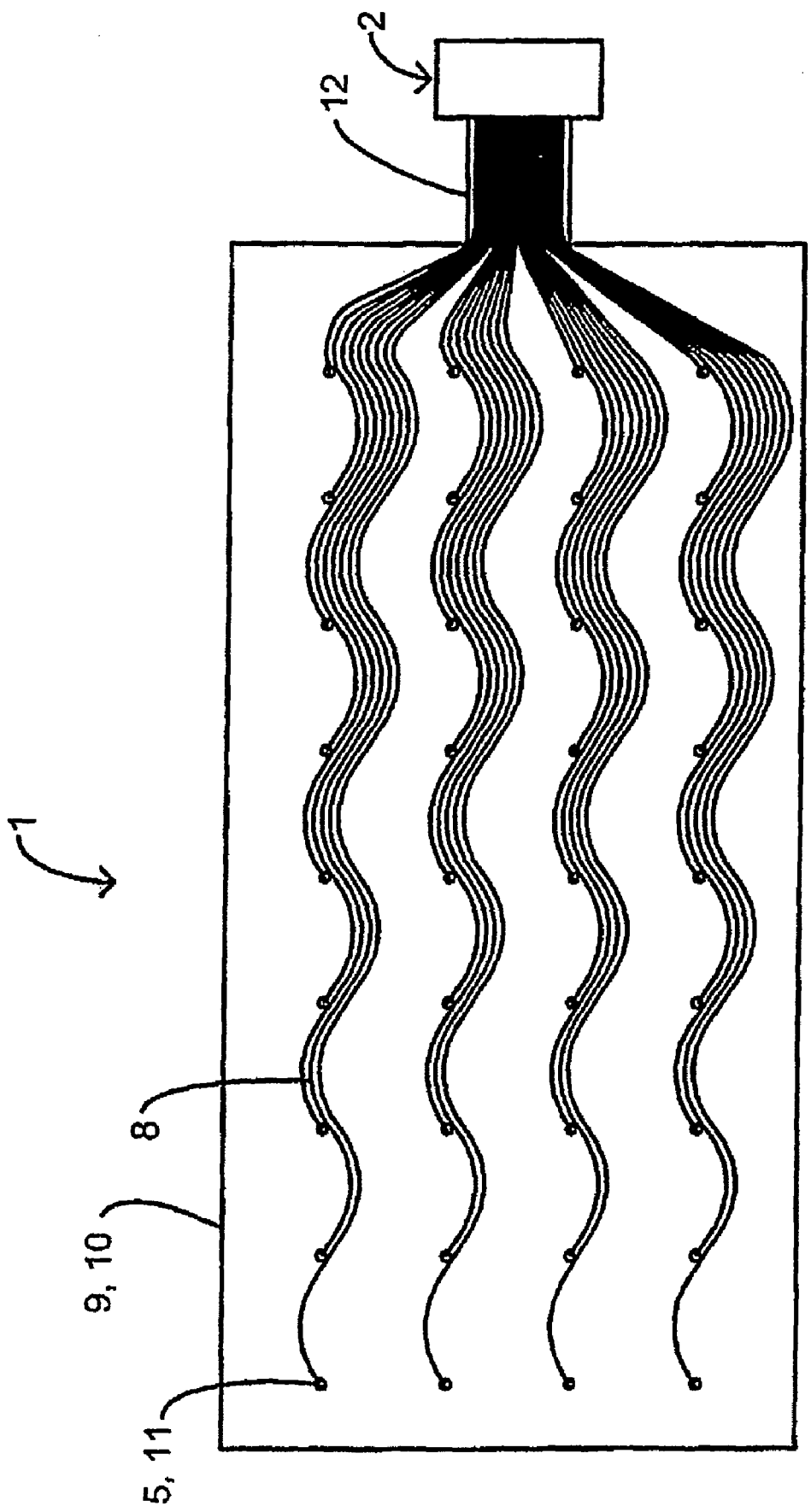
FIG. 6 shows a pressure sensitive member and interface electronics according to one embodiment of the invention.
Figure 7A:
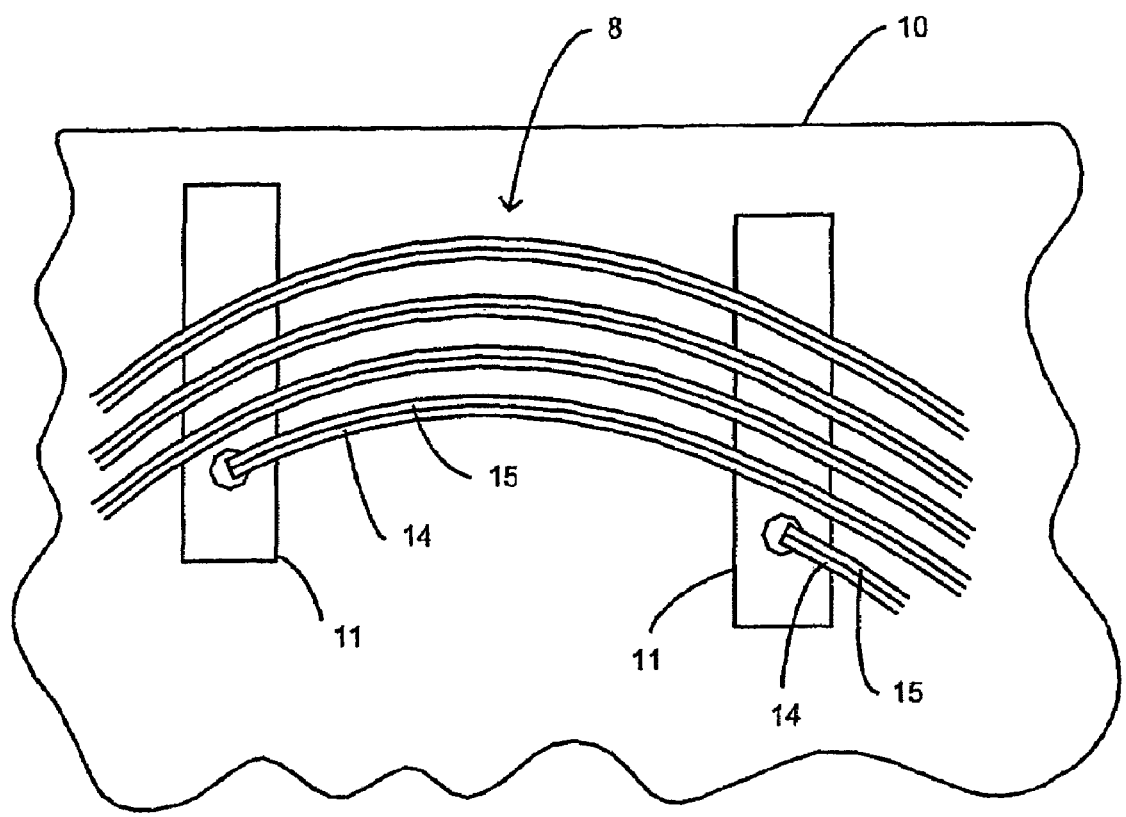
FIG. 7(a) shows a top view of a portion of the pressure sensitive member of FIG. 2, with the top layer removed.
Figure 7B:
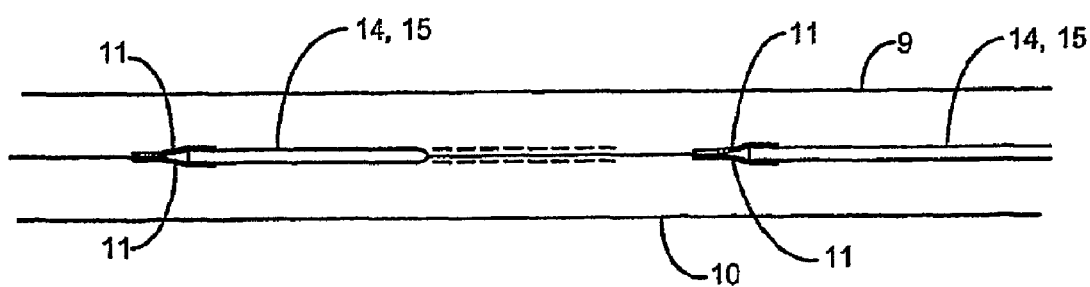
FIG. 7(b) is a cross-sectional view of the portion of the pressure sensitive member of FIG. 3(a), with the top layer present.
Figure 9:
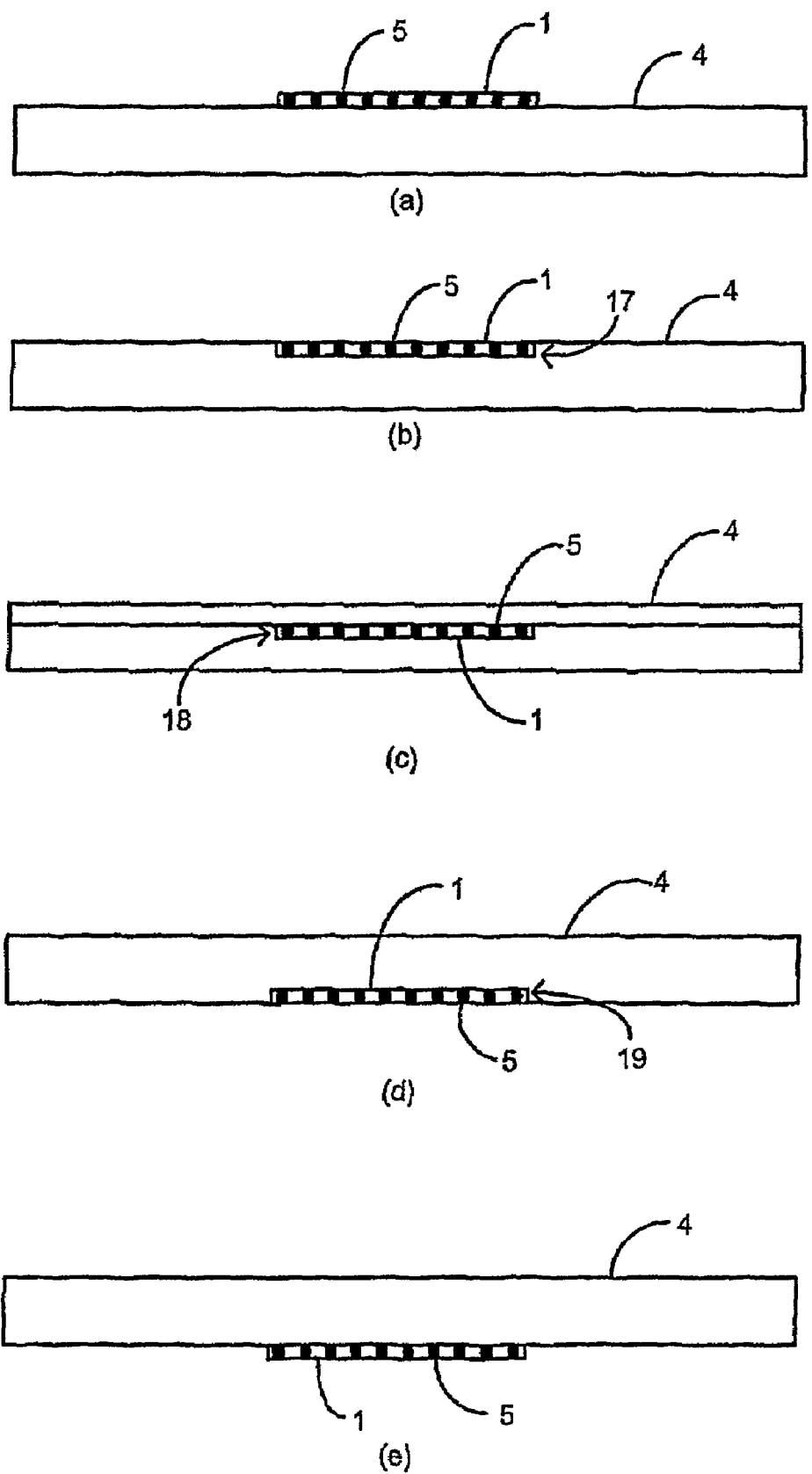
FIG. 9(a) illustrates an embodiment of the invention wherein the pressure sensitive member is coupled to the top of a support member.
FIG. 9(b) illustrates an alternative embodiment of the invention wherein the pressure sensitive member is coupled within a recess in a top surface of the support member.
FIG. 9(c) illustrates an alternative embodiment of the invention wherein the pressure sensitive member is coupled within a cavity within the support member.
FIG. 9(d) illustrates an alternative embodiment of the invention wherein the pressure sensitive member is coupled within a recess in a bottom surface of the support member.
FIG. 9(e) illustrates an alternative embodiment of the invention wherein the pressure sensitive member is coupled to the bottom of the support member; and, FIG. 10 illustrates an alternative embodiment of the invention wherein pressure sensors are arranged into three groups within the pressure sensitive member.

FIGS. 6, 7(a) and 7(b) illustrate a pressure sensitive member 1 according to one embodiment of the invention. Pressure sensitive member 1 comprises a plurality of Kinotex™ pressure sensors 5 sandwiched between two layers 9, 10 of a compressible material. The compressible material may comprise foam, and preferably comprises a soft polyurethane foam. Preferably, several bundles of plastic optical fibres 8 deliver and retrieve the light energy from interface electronics 2 to pressure sensors 5. The bundles of fibre 8 are preferably gathered and optionally passed through a protective sleeve 12 that terminates at the interface electronics 2. The bundles of fibre 8 preferably each comprise a plurality of fibre pairs 14, 15. An area of adhesive 11 is preferably used to secure each fibre pair 14, 15 to the layers 9, 10 above and below each pressure sensor 5. In embodiments wherein pressure sensitive member is to be located at the top of or within support member 4, as shown in FIGS. 9(a)-(c), fibre bundles 8 are preferably arranged sinusoidally between layers 9, 10 and not adhered along their length so as to provide some flexibility and resilience to pressure sensitive member 1. In embodiments wherein pressure sensitive member 1 is to be located at the bottom of support member 4, as shown in FIG. 9(d)-(e), fibre bundles 8 may be adhered along their entire length, as pressure sensitive member 1 will preferably be adjacent to or mounted on a rigid surface.

Top layer 9 and bottom layer 10 are preferably constructed from material chosen to be suitable with the specific characteristics of pressure sensors 5. Materials well suited for use with Kinotex™ pressure sensors are structurally self-supporting, compressible, at least partially transmissive of light, and optionally elastically resilient. The inventors have determined that white or natural-coloured low density polyurethane foam are suitable materials for use with Kinotex™ pressure sensors. Such foam is available from, among others, Lendell Manufacturing Inc. of St. Charles, Mich., product code HSS. The inventors have also determined that most standard bed mattress foam materials can be used as top layer 9 and/or bottom layer 10. It will be understood that many different foam materials provide similar characteristics and the present invention is not limited to a specific material. A covering material (not shown) which is opaque at wavelengths used by pressure sensors 5 is preferably provided to keep ambient light from disturbing the Kinotex™ pressure sensors. The opaque covering material preferably comprises a two-tone flexible plastic cover that is black on the inside and white on the outside, which envelops pressure sensitive member 1.

Figure 8:
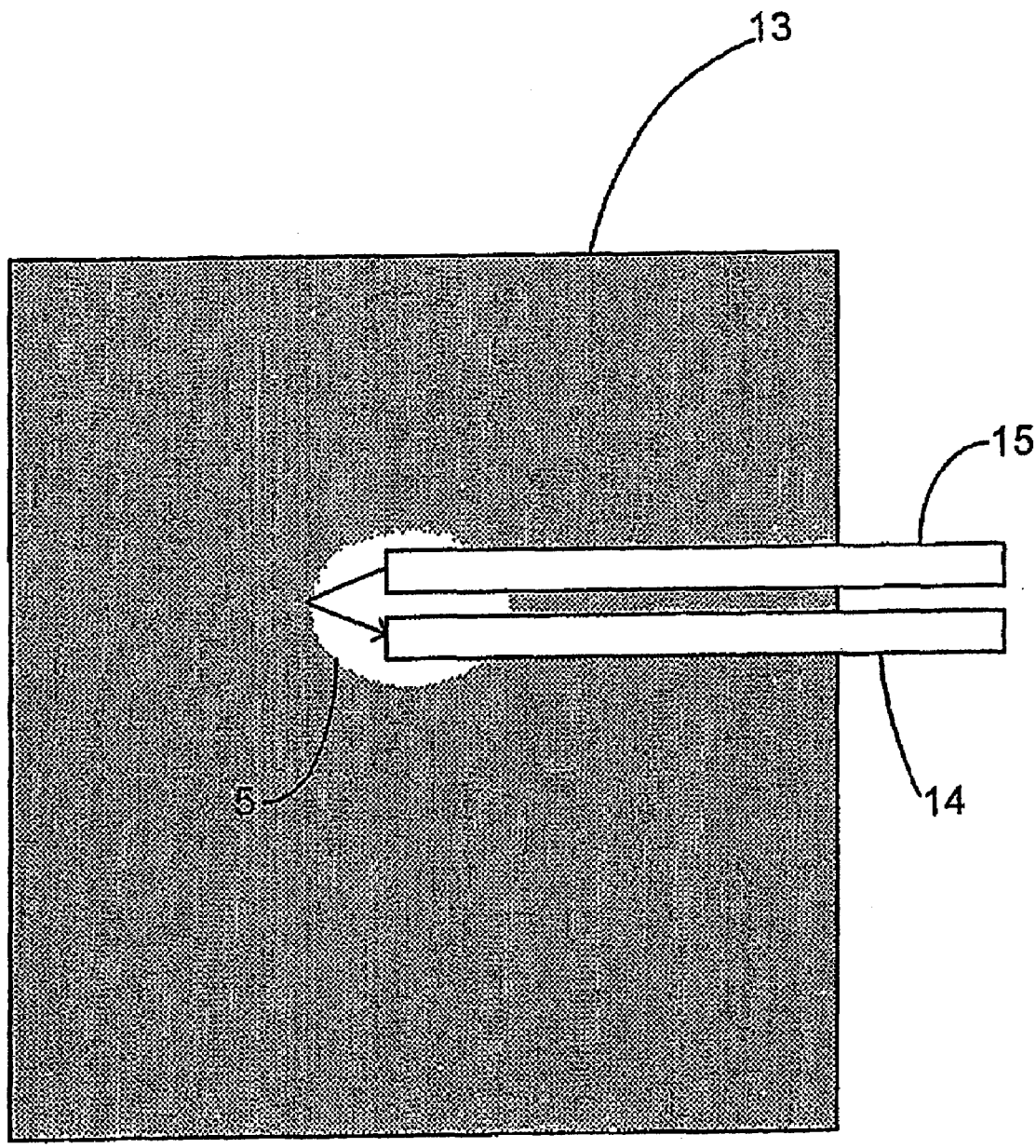
FIG. 8 is a sectional view of a portion of a mattress with a pair of fibres inserted therein according to another embodiment of the invention.

In an alternative embodiment, pressure sensitive member 1 comprises an area of the mattress in which pressure sensors 5 are formed. FIG. 8 illustrates a section of mattress 13 with input and output fibres 15, 14 inserted therein. The compressible material of mattress 13, in addition to supporting bed occupant 6 (not shown in FIG. 8), reflects incident wave energy received from input fibre 15 to output fibre 14, and thus forms pressure sensors 5. The FIG. 8 embodiment is particularly advantageous for equipping an existing bed with a bed occupant monitoring system 7 according to the invention, as one may do so by simply inserting optical fibres into the mattress.

Pressure sensitive member 1 is preferably flexible and soft. Pressure sensitive member 1 can be placed on a support member 4, which may comprise a bed mattress, underneath the sheets and coverings upon which bed occupant 6 lies. The inventors have determined that, where soft sensors such as Kinotex™-type sensors are used, pressure sensitive member 1 can be made to be essentially undetectable to a bed occupant 6. In some embodiments, the deformable material of sensors 5 has an elastic modulus which is substantially the same as that of the material surrounding sensors 5.

It must be understood that FIG. 1 is a schematic representation of one possible embodiment of the invention. Many variations in the physical locations and sizes of the elements are possible. For example, among other things, the pressure sensitive member 1 may be located in-between occupant 6 and support member 4, or it may be embedded in support member 4. Some of the possible positions for pressure sensitive member 1 are shown in FIGS. 9(a)-(e). FIGS. 9(a) to 9(e) illustrate various embodiments of the invention with pressure sensitive member 1 placed in different positions with respect to support member 4. FIG. 9(a) illustrates an embodiment wherein pressure sensitive member 1 is on top of support member 4. FIG. 9(b) illustrates an embodiment wherein pressure sensitive member 1 is placed in a recess 17 near the top of support member 4 so that the top of member 1 is flush with the top surface of support member 4. FIG. 9(c) illustrates an embodiment wherein support member 4 is made of at least two layers laminated together, between which is sandwiched pressure sensitive member 1 within a cavity 18. FIG. 9(d) illustrates an embodiment wherein pressure sensitive member 1 is located in a recess 19 near the bottom of support member 4 so that the bottom of member 1 is flush with the bottom surface of support member 4. FIG. 9(e) illustrates an embodiment wherein pressure sensitive member 1 is attached to the bottom of support member 4.

The wide dynamic range of Kinotex™-type sensors permits such sensors to pick up usable signals even when pressure sensitive member 1 is located under or within a mattress.

Although many arrangements of pressure sensors 5 are possible, pressure sensors 5 may conveniently be arranged in a rectangular array extending across the width of support member 4. Pressure sensors 5 may be spaced approximately 2 cm to 10 cm apart. Depending on the intended application, the array of pressure sensors 5 may extend the entire length of support member 4 or some portion of the length. For example, to monitor the bed occupant's respiration, the inventors have found that a 60-sensor array approximately 90 cm wide by 30 cm in length is sufficient. A larger device with correspondingly more sensors may be used for larger occupants.

Figure 10:
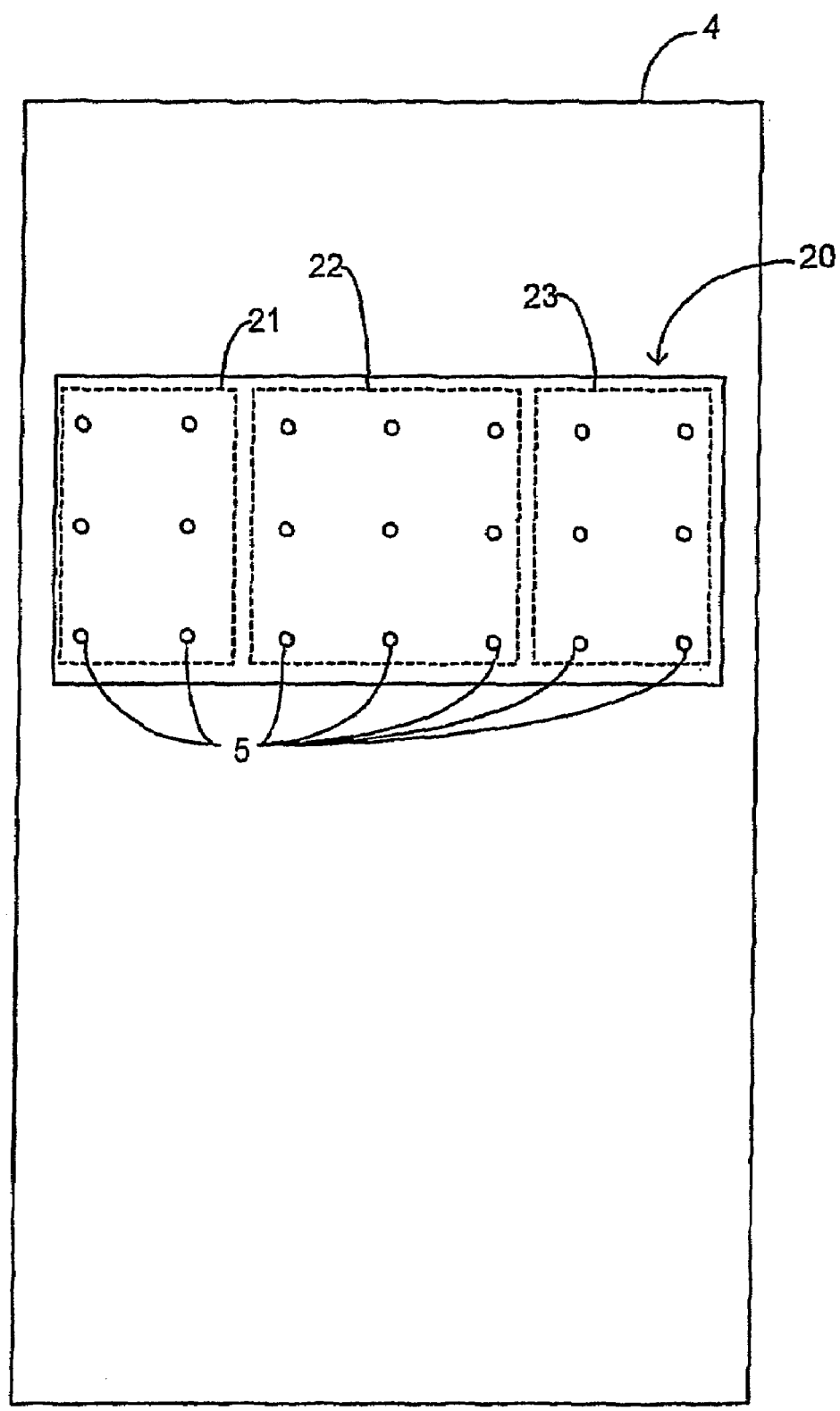

FIG. 10 illustrates a pressure sensitive member 20 according to an embodiment of the invention wherein pressure sensors 5 are arranged into three groups 21, 22 and 23. Pressure sensitive member 20 of FIG. 10 is dimensioned so that it spans the width of support member 4, with side groups 21 and 23 adjacent to the edges of support member 4. The responses of all of the pressure sensors 5 within the central group 22 are summed by interface electronics 2 by using a single photo-sensor (not shown in FIG. 5) to detect their light output simultaneously. Pressure applied to any pressure sensor 5 within central group 22 will result in a change in an output signal from interface electronics 2 which is representative of the average pressure on the sensors of central group 22. In a similar manner, the signals from pressure sensors 5 in side groups 21 and 23 are summed using a second photo-sensor (not shown). This results in two output signals: one representing the total pressure applied within central group 22, and another representing the pressure applied within side groups 21 and 23.

Interface electronics 2 may also comprise further analog electronics to compare these signals to produce a third signal that is derived therefrom. The third signal indicates three possible states: 1) there is no occupant in the bed (determined by both first and second signals being below a threshold); 2) the bed occupant is in the central region (determined by the first signal being above a first threshold and the second signal being below a second threshold); 3) the bed occupant is near the edge of the bed (determined by the second signal being above the second threshold). Interface electronics can be used to active an audible alarm or an attendant call system depending on which of the three states is indicated by the third signal, and on predetermined monitoring parameters.

As will be apparent to those skilled in the art in the light of the foregoing disclosure, many alterations and modifications are possible in the practice of this invention without departing from the scope thereof. Accordingly, the scope of the invention is to be construed in accordance with the substance defined by the following claims.

What is claimed is:

1. A bed occupant monitoring system comprising:
   a first grouping of spaced-apart fiber-optic pressure sensors configured to generate first light output in response to pressure applied to a first portion of a mattress,
   a second grouping of spaced-apart fiber-optic pressure sensors configured to generate second light output in response to pressure applied to a second portion of the mattress spaced from the first portion of the mattress, and
   electronics, spaced from the first and second groupings of fiber-optic pressure sensors, including:
      at least one first light source to provide light energy to the first grouping of fiber-optic pressure sensors,
      at least one first light sensor to detect the first light output from the first grouping of fiber-optic pressure sensors and generate a first electrical signal indicative of pressure applied to one or more of the pressure sensors in the first grouping of fiber-optic pressure sensors,
      at least one second light source to provide light energy to the second grouping of fiber-optic pressure sensors,
      at least one second light sensor to detect the second light output from the second grouping of fiber-optic pressure sensors and generate a second electrical signal indicative of pressure applied to one or more of the pressure sensors in the second grouping of fiber-optic pressure sensors, and
      circuitry to determine a total pressure applied to the mattress, determine a first pressure applied to the first portion of the mattress, and determine a second pressure applied to the second portion of the mattress, from the first and second electrical signals, and send the first pressure, second pressure, and total pressure to a remote monitoring station.

2. The system of claim 1, wherein each pressure sensor includes an input optical fiber configured to provide light energy from the electronics to the pressure sensor and an output optical fiber configured to return light energy from the pressure sensor to the electronics.

3. The system of claim 2, wherein the input and output optical fibers are non-coupled.

4. The system of claim 2, wherein each of the input optical fibers of the first grouping of pressure sensors is coupled to the at least one first light source and each of the output optical fibers of the first grouping of pressure sensors is coupled to the at least one first light sensor.

5. The system of claim 4, wherein each of the input optical fibers of the second grouping of pressure sensors is coupled to the at least one second light source and each of the output optical fibers of the second grouping of pressure sensors is coupled to the at least one second light sensor.

6. The system of claim 2, wherein the electronics includes the at least one first light source and the at least one second light source each coupled to an input fiber and the at least one first light sensor and the at least one second light sensor each coupled to an output optical fiber.

7. The system of claim 2, wherein each pressure sensor includes compressible material adjacent the input and output optical fibers.

8. The system of claim 7, wherein the compressible material is configured to support a bed occupant and the compressible material is configured to reflect incident wave energy provided by the input optical fiber.

9. The system of claim 1, including a third grouping of spaced-apart fiber-optic pressure sensors configured to generate third light output in response to pressure applied to a third portion of a mattress spaced from the first and second portions of the mattress.

10. The system of claim 9, wherein the third grouping of spaced-apart fiber-optic pressure sensors is positioned between the first and second groupings of spaced-apart fiber-optic pressure sensors.

11. The system of claim 10, comprising a third light source coupled to the third grouping of fiber-optic pressure sensors and a third light sensor coupled to the third grouping of fiber-optic pressure sensors.

12. The system of claim 1, wherein the electronics are configured to process the light output of the pressure sensors in the first grouping of fiber-optic pressure sensors substantially simultaneously such that pressure applied to any of the pressure sensors in the first grouping modifies the first electrical signal.

13. The system of claim 1, wherein the electronics are configured to produce a third signal including an indicator of at least one of a plurality of possible states including a first state representative of no bed occupant, a second state representative of a bed occupant being positioned in a central portion of the mattress, and a third state representative of a bed occupant being positioned near an edge of the mattress.

14. The system of claim 1, wherein the electronics includes circuitry for comparing the first and/or second electrical signals to a predetermined threshold, a comparer to determine if the first and/or second electrical signals are below the predetermined threshold, a threshold crossing detector configured to reset a timer when the first and/or second electrical signals cross the predetermined threshold, and an alarm signal generator configured to generate an alarm signal if the timer is not reset for a predetermined time period and the first and/or second electrical signals are below the predetermined threshold.

15. A bed occupant monitoring system comprising:
   a support member configured to support at least a portion of a person,
   a plurality of spaced-apart groups of optical pressure sensors, each group configured to sense pressure applied to a different area of the support member, each group having a first end proximate a portion of the support member and a second end spaced from the first end, and electronics coupled to the second end of each group and spaced from the first end of each group, the electronics including a microprocessor configured to generate output signals corresponding to light intensities received from at least one of the pressure sensors, each of the output signals being representative of a sum of a time derivative of pressure values sensed by the pressure sensors of one of the groups of pressure sensors.

16. The system of claim 15, wherein each pressure sensor includes an optical fiber pair, each optical fiber pair includes an input fiber and an output fiber, each of the input and output fibers have a first end spaced from the support member and a second end operably coupled to a portion of the support member, the first ends of the input and output fibers are substantially adjacent one another and the second ends of the input and output fibers are substantially adjacent one another, and the electronics are coupled to the first ends of the input and output fibers of each optical fiber pair and spaced from the second ends of the input and output fibers.

17. The system of claim 16, comprising a user interface operably coupled to the electronics to configure a bodily movement threshold determiner for differences in weights and movement patterns of different bed occupants.

18. The system of claim 15, wherein the electronics includes a bodily movement threshold determiner configured to determine whether output signals have remained below a bodily movement threshold for a period of time sufficient to activate an alarm.

19. The system of claim 18, wherein the determiner determines whether one of the output signals includes a pulmonary alarm indicative of suspension of pulmonary activity.

20. A bed occupant monitoring system comprising:
a mattress adapted to support at least a portion of a bed occupant,
a pressure sensitive member coupled to the mattress and arranged to lie below a top surface of the mattress, the pressure sensitive member including a plurality of spaced-apart pressure sensors configured to send pressure signals corresponding to pressure applied to the pressure sensitive member,
electronics operably coupled to the pressure sensors to receive the pressure signals and configured to analyze at least one of magnitude, frequency and variations in the pressure signals over time to determine at least one of heart rate, bodily movement, and pulmonary activity of the bed occupant and differentiate the signals as being representative of heart rate, pulmonary activity, and bodily movement, and
a user interface operably coupled to the electronics and configured to transmit input signals to the electronics, the input signals being indicative of differences in at least one of a threshold value relating to the at least one of heart rate, bodily movement, and pulmonary activity, and a time period relating to the at least one of heart rate, bodily movement, and pulmonary activity, and to graphically indicate the signals representative of heart rate, pulmonary activity or bodily movement.

21. The system of claim 20, wherein the user interface enables adjustment by a user of at least one of a pulmonary activity threshold, a pulmonary activity time period, a bodily movement threshold, a bodily movement time period, a heart rate threshold, and a heart rate time period.

22. The system of claim 21, wherein the electronics are configured to generate an alarm indicative of a change in at least one of the heart rate, bodily movement, and pulmonary activity of the bed occupant.

\* \* \* \* \*

UNITED STATES PATENT AND TRADEMARK OFFICE
CERTIFICATE OF CORRECTION

| | |
|---|---|
| PATENT NO. | : 7,825,814 B2 |
| APPLICATION NO. | : 12/017605 |
| DATED | : November 2, 2010 |
| INVENTOR(S) | : David M. Lokhorst and D. Robert Inkster |

It is certified that error appears in the above-identified patent and that said Letters Patent is hereby corrected as shown below:

On the Title page of the patent please delete Item (73) in its entirety.

Signed and Sealed this
Fifteenth Day of March, 2011

David J. Kappos
*Director of the United States Patent and Trademark Office*